United States Patent
Ostrow et al.

(10) Patent No.: US 8,204,592 B1
(45) Date of Patent: Jun. 19, 2012

(54) SYSTEM AND METHOD FOR GENERATING AND USING CARDIAC ISCHEMIA DIAGNOSTICS BASED ON ARRHYTHMIA PRECURSORS AND ARRHYTHMIA EPISODES

(75) Inventors: Eliot L. Ostrow, Sunnyvale, CA (US); Jay Snell, Studio City, CA (US); Xiaoyi Min, Thousand Oaks, CA (US)

(73) Assignee: Pacesetter, Inc., Sylmar, CA (US)

(*) Notice: Subject to any disclaimer, the term of this patent is extended or adjusted under 35 U.S.C. 154(b) by 519 days.

(21) Appl. No.: 11/949,532

(22) Filed: Dec. 3, 2007

(51) Int. Cl.
*A61N 1/36* (2006.01)

(52) U.S. Cl. .......... 607/14; 600/508; 600/509; 600/515; 607/9

(58) Field of Classification Search .......... 600/508–509, 600/513, 515; 607/9, 14
See application file for complete search history.

(56) References Cited

U.S. PATENT DOCUMENTS

| | | | |
|---|---|---|---|
| 5,113,869 A * | 5/1992 | Nappholz et al. ............. 600/508 |
| 5,135,004 A | 8/1992 | Adams et al. |
| 5,199,428 A | 4/1993 | Obel et al. |
| 5,203,326 A | 4/1993 | Collins |
| 5,313,953 A | 5/1994 | Yomtov et al. |
| 5,328,460 A | 7/1994 | Lord et al. |
| 6,016,443 A | 1/2000 | Ekwall et al. |
| 6,021,350 A | 2/2000 | Mathson |
| 6,108,577 A | 8/2000 | Benser |
| 6,112,116 A | 8/2000 | Fischell et al. |
| 6,115,628 A * | 9/2000 | Stadler et al. ............. 600/517 |
| 6,128,526 A * | 10/2000 | Stadler et al. ............. 600/517 |
| 6,233,486 B1 | 5/2001 | Ekwall et al. |
| 6,256,538 B1 | 7/2001 | Ekwall |
| 6,264,606 B1 | 7/2001 | Ekwall et al. |
| 6,272,379 B1 | 8/2001 | Fischell et al. |
| 6,381,493 B1 | 4/2002 | Stadler et al. |
| 6,501,983 B1 | 12/2002 | Natarajan et al. |
| 6,622,045 B2 | 9/2003 | Snell et al. |
| 6,778,852 B2 | 8/2004 | Galen et al. |
| 7,076,298 B2 * | 7/2006 | Padmanabhan et al. ........ 607/14 |
| 7,225,015 B1 | 5/2007 | Min et al. |
| 7,274,959 B1 | 9/2007 | Wang et al. |
| 2003/0176802 A1 | 9/2003 | Galen et al. |
| 2004/0138716 A1 | 7/2004 | Kon et al. |
| 2004/0215289 A1 * | 10/2004 | Fukui ............................ 607/48 |
| 2007/0118178 A1 * | 5/2007 | Fukui ............................ 607/9 |

* cited by examiner

*Primary Examiner* — Niketa Patel
*Assistant Examiner* — Joseph Stoklosa

(57) ABSTRACT

Techniques are described for generating diagnostic information to aid in determining whether cardiac ischemia within a patient is clinically actionable. In one example, a pacemaker or implantable cardioverter/defibrillator (ICD) detects information pertaining to arrhythmia precursors and to episodes of sustained arrhythmias, as well as information pertaining to episodes of cardiac ischemia. The implanted device then correlates the arrhythmia precursors and the sustained arrhythmias with the episodes of cardiac ischemia so as to generate diagnostics permitting a physician reviewing the diagnostics to determine whether the ischemia is clinically actionable. In some implementations, the diagnostics are instead generated by an external system based on raw data provided by the implanted device. In some implementations, the device itself determines whether the ischemia is clinically actionable and automatically controls therapy or generates warning signals accordingly.

7 Claims, 10 Drawing Sheets

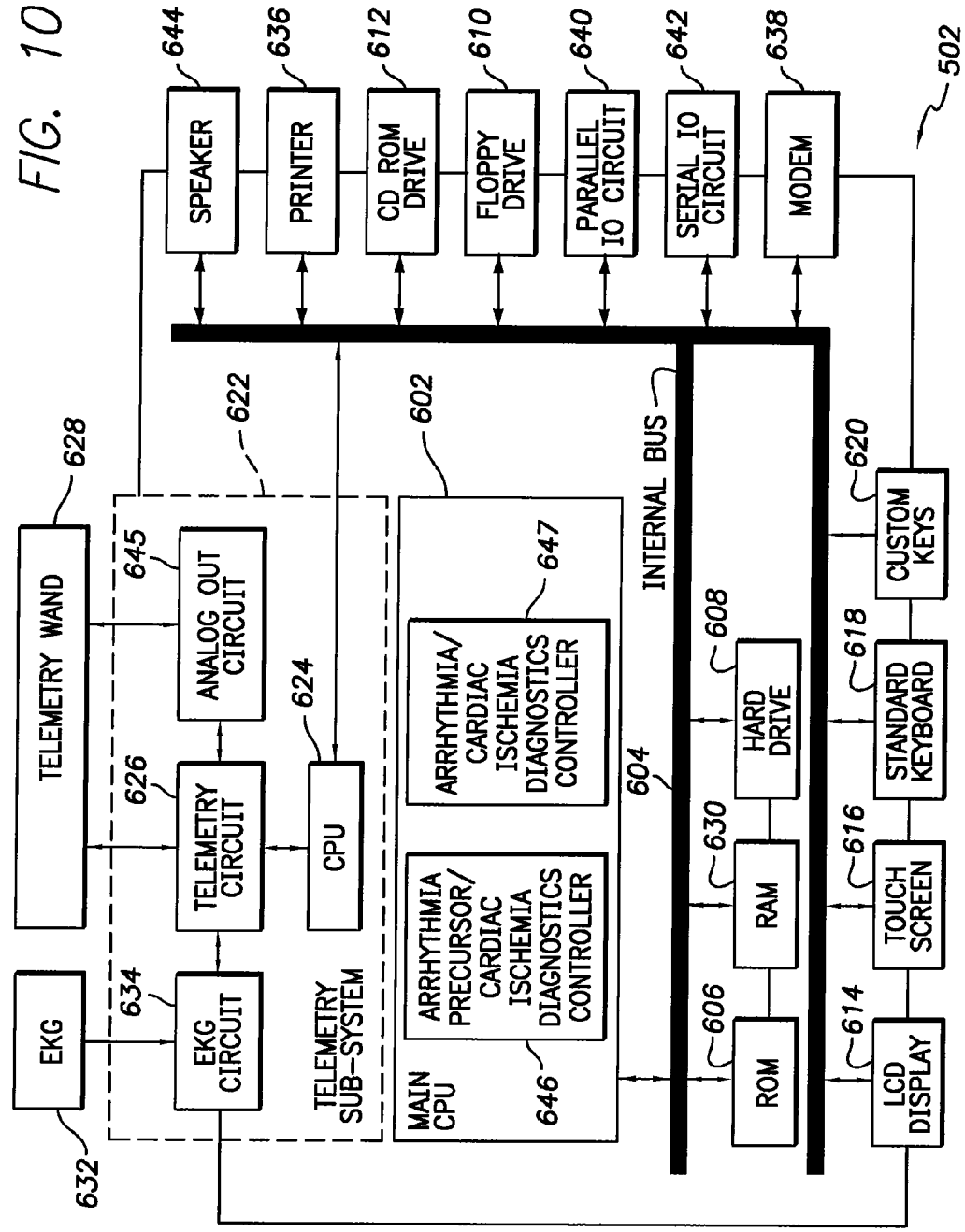

US 8,204,592 B1

SYSTEM AND METHOD FOR GENERATING AND USING CARDIAC ISCHEMIA DIAGNOSTICS BASED ON ARRHYTHMIA PRECURSORS AND ARRHYTHMIA EPISODES

FIELD OF THE INVENTION

The invention generally relates to implantable medical devices such as pacemakers and implantable cardioverter/defibrillators (ICDs) and to external devices for use therewith and, in particular, to techniques for generating diagnostics pertaining to cardiac ischemia using such devices.

BACKGROUND OF THE INVENTION

Cardiac ischemia is a condition whereby heart tissue does not receive adequate amounts of oxygen and is usually caused by the narrowing or blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to complete or non-complete blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death here in the United States and worldwide. In some cases, although the AMI itself is not fatal, it strikes while the victim is engaged in potentially dangerous activities, such as driving vehicles or flying airplanes, and the severe pain and possible loss of consciousness associated with AMI results in fatal accidents. Even if the victim survives the AMI, quality of life may thereafter be severely restricted. Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) where the ventricles of the heart beat chaotically, resulting in little or no net flow of blood from the heart to the brain and other organs.

Many patients at risk of cardiac ischemia have pacemakers, ICDs or other medical devices implanted therein, or are candidates for such devices. Accordingly, techniques have been developed for using the implanted medical device to generate diagnostic information pertaining to ischemia for subsequent review by a physician or other clinician. That is, the diagnostic information is transmitted from the implanted device to a bedside monitor, external programmer or other external device, which displays the diagnostic information to the physician. The physician then reviews the information to determine whether the ischemia is "clinically actionable", i.e. whether medical intervention is warranted. For example, the diagnostics might specify an "ischemic burden", which is representative of a change in duration and/or severity of ischemic events over time as determined, e.g., based on changes in ST segment elevations within an intracardiac electrogram (IEGM). If the ischemic burden increases significantly within a particular patient, medical intervention might be necessary.

However, various other factors are preferably considered by the physician along with duration and severity of episodes of ischemia when determining whether the ischemia is clinically actionable. Accordingly, it would be desirable to provide diagnostic systems capable of generating enhanced ischemia diagnostics that additionally provide information pertaining to these other factors. It is to this end that aspects of the present invention are directed.

Some implantable systems are programmed to directly detect cardiac ischemia based on ST segments and to immediately generate ischemia warning signals for alerting the patient. That is, the implanted device does not merely generate ischemia diagnostics for subsequent review, but actually detects the onset of episodes of ischemia so that warnings can be promptly generated. Some such systems automatically control or adjust therapy in response to the ischemia as well. See, for example, U.S. Pat. No. 6,108,577 to Benser, entitled "Method and Apparatus for Detecting Changes in Electrocardiogram Signals". See, also, U.S. Pat. Nos. 5,113,869 to Nappholz; 5,135,004 to Adams et al.; 5,199,428 to Obel et al.; 5,203,326 to Collins; 5,313,953 to Yomtov et al; 6,501,983 to Natarajan, et al.; 6,016,443, 6,233,486, 6,256,538, and 6,264,606 to Ekwall; 6,021,350 to Mathson; 6,112,116 and 6,272,379 to Fischell et al; 6,128,526, 6,115,628 and 6,381,493 to Stadler et al.

As noted, however, there are various other factors, discussed below, that are preferably considered before determining whether cardiac ischemia is clinically actionable. Accordingly, those factors ought to be taken into account by the physician in the management of the patient. Hence, it would be desirable to provide implantable devices with the capability of generating diagnostics for physician review that take the additional factors into account. It is to this end that aspects of the present invention are primarily directed. Also, if the implantable device itself is equipped to generate warnings and control therapy in response to ischemia, such factors ought to be taken into account by the implanted device as well. Accordingly, it would also be desirable to provide implantable devices that are capable of considering these factors before generating warnings or delivering therapy. It is to this end that still other aspects of the present invention are directed.

SUMMARY OF THE INVENTION

In a first general embodiment, enhanced cardiac ischemia diagnostics are generated that take into account arrhythmia precursors, such as premature ventricular contractions (PVCs), premature atrial contractions (PACs) and episodes of non-sustained supraventricular tachycardia (SVT). In one example, the enhanced cardiac ischemia diagnostics are generated by a pacemaker or other implantable medical device and then transmitted to an external system for review by a physician. The enhanced diagnostics allow the physician to make a more informed judgment as to whether episodes of cardiac ischemia are clinically actionable. In other examples, the device itself uses the enhanced diagnostics to determine whether to generate warning signals for alerting the patient or whether to automatically deliver therapy. Note that arrhythmia precursors such as PVCs and PACs do not necessarily cause or trigger either an arrhythmia or an ischemia. Nevertheless, it is helpful to provide diagnostic information relating arrhythmia precursor events with ischemic events within a patient, as such information can aid the physician in determining whether ischemia within the patient is clinically actionable.

In an illustrative example, a pacemaker or ICD detects arrhythmia precursor events within the patient and also detects episodes of cardiac ischemia within the patient. The device generates diagnostics relating the arrhythmia precursor events with the episodes of cardiac ischemia and then controls at least one device function based on the diagnostics, such as controlling the recording of the diagnostics in memory, controlling the generation of warning signals, or controlling the delivery of pacing or other therapy. The detected arrhythmia precursor events can include ventricular arrhythmia precursors such as PVCs and episodes of non-sustained ventricular tachycardia (NSVT), as well as supraventricular arrhythmia precursors such as PACs and episodes of non-sustained SVT. Preferably, the device distinguishes among lone precursor events, couplets of precursor events and runs of precursor events having three or more events in sequence. The device also evaluates the relative severity of individual episodes of cardiac ischemia and also tracks the time of day when arrhythmia precursors and episodes of cardiac ischemia occur.

The device then generates and records diagnostic information that tracks and distinguishes arrhythmia precursor events based on: precursor type (ventricular vs. supraventricular); precursor duration (lone, couplet, runs of 3-5 beats, runs of 6-10 beats, etc.); the rate of precursor events; the presence or absence of ischemia; the severity of ischemia; and/or the time of day. Changes over time in these parameters are also tracked such as: changes in the rate at which precursor events occur; changes in the ratio of lone precursors events to runs of precursor events; change in the ratio of arrhythmia precursor events occurring during episodes of ischemia as compared to precursor events occurring during episodes without ischemia; and changes in the durations of individual precursor events, such as the durations of episodes of non-sustained SVT. The diagnostics are then transmitted to an external device for physician review. (Alternatively, the raw data detected by the implanted device is transmitted to the external device, which generates the ischemia diagnostics therein.) Preferably, the physician can control the specific information to be displayed so as to highlight information that he or she finds particularly helpful in deciding whether the ischemia is clinically actionable. In this regard, arrhythmias precursors may be harbingers of sustained, potentially lethal arrhythmias. Hence, any information pertaining to the association of precursor events with ischemic episodes may make clinical intervention to address the ischemia (e.g., angioplasty, coronary artery bypass graft (CABG), etc.) more urgent. Similarly, if the ischemic events only occur when tachycardias occur, then the physician may choose to adjust prescribed medications, upgrade from a pacer to an ICD, etc., to address the tachycardias so as to, in turn, reduce ischemia within the patient.

In a second general embodiment, enhanced cardiac ischemia diagnostics are generated that take into account whether episodes of sustained arrhythmia precede episodes of cardiac ischemia or follow the ischemia, i.e. whether arrhythmias are pre-ischemia or post-ischemia. Herein, a sustained arrhythmia is one that continues until terminated by therapy. A non-sustained arrhythmia is one that terminates on its own. A pre-ischemia arrhythmia is an arrhythmia that begins prior to the onset of an episode of ischemia. A post-ischemia arrhythmia is an arrhythmia that beginnings following the onset of an episode of ischemia, and thus includes arrhythmias that begin sometime during an ischemia episode. Pre-ischemia arrhythmias may also be referred to as "pre-ischemia onset arrhythmias." Likewise, post-ischemia arrhythmias may also be referred to as "post-ischemia-onset arrhythmias." The onset of an episode of ischemia may be defined as the point at which a parameter indicative if ischemia (e.g. ST segment deviation) crosses a detection threshold.

In an illustrative example, a pacemaker or ICD detects episodes of arrhythmia within the patient and also detects episodes of cardiac ischemia. The device distinguishes episodes of arrhythmia that precede episodes of cardiac ischemia (i.e. arrhythmias that might be a proximate cause of the ischemia) from episodes of arrhythmia that follow episodes of cardiac ischemia (i.e. arrhythmias that might have been caused by the ischemia). The device then generates diagnostics relating the arrhythmias with the episodes of cardiac ischemia and distinguishing the episodes of arrhythmia that precede cardiac ischemia from the episodes that follow cardiac ischemia. The device controls at least one device function based on the diagnostics, such as controlling the recording of the diagnostics in memory, controlling the generation of warning signals, or controlling the delivery of pacing or other therapy. The arrhythmias to be detected include both sustained ventricular arrhythmias and sustained supraventricular arrhythmias. Examples of sustained ventricular arrhythmias include: sustained ventricular tachycardia (VT); and VF. Examples of sustained supraventricular arrhythmias include: sustained SVT; sustained atrial tachycardia (AT); atrial fibrillation (AF); and atrial flutter. Preferably, as with the arrhythmia precursor examples above, the device also evaluates the relative severity of individual episodes of cardiac ischemia and also tracks the time of day when episodes of arrhythmia and episodes of cardiac ischemia occur.

Based on this sustained arrhythmia information, the device then generates and records diagnostic information that tracks and distinguishes sustained arrhythmias based on whether the arrhythmias precede or follow episodes of ischemia, and further based on: the general type of arrhythmia (ventricular vs. supraventricular); the specific type of arrhythmia (VT vs. VF, etc.); the severity of the ischemia; and/or the time of day. Changes over time in these parameters are also tracked such as: changes in the rate at which sustained arrhythmias occur; changes in the ratio of sustained arrhythmias that precede ischemia to those that follow ischemia; and changes in the durations of sustained arrhythmias, such as the durations of episodes of sustained SVT or sustained atrial flutter. The diagnostics are then transmitted to an external device for physician review. Alternatively, as noted above, raw data detected by the implanted device is transmitted to the external device, which generates the diagnostics therein.

Preferably, the enhanced cardiac ischemia diagnostics generated by the system take into account both arrhythmia precursors and sustained arrhythmias, i.e., both of the techniques summarized above are implemented within the same system thereby providing the physician (or the implanted device itself) with a wealth of information for evaluating cardiac ischemia. As already noted, the device itself may be programmed to evaluate enhanced diagnostics to determine whether to issue warning signals and/or control therapy. Warning signals can include both "tickle warning" signals applied to subcutaneous tissue and short-range telemetry warning signals transmitted to a warning device external to the patient. Therapy depends upon the capabilities of the implanted system. In one example, if the implanted system is equipped with a drug pump, appropriate medications may be administered in response to cardiac ischemia, particularly anti-thrombolytic drugs. If overdrive pacing is being applied by the system, the overdrive pacing is preferably deactivated to prevent the increased heart rate associated with overdrive pacing from exacerbating cardiac ischemia. If the system has defibrillation capabilities, the system may be programmed to immediately begin charging defibrillation capacitors upon detection of cardiac ischemia to permit prompt delivery of a defibrillation shock if the ischemia triggers VF.

Hence, techniques are provided for generating and using enhanced cardiac ischemia diagnostics. System and method implementations of the techniques are described herein.

BRIEF DESCRIPTION OF THE DRAWINGS

The above and further features, advantages and benefits of the present invention will be apparent upon consideration of the present description taken in conjunction with the accompanying drawings, in which:

FIG. 10 is a functional block diagram illustrating components of an external programmer for use with pacer/ICD of FIGS. 8 and 9, and in particular illustrating programmer-based components for generating cardiac ischemia diagnostics also in accordance with the techniques of FIGS. 2-6.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable System

Figure 1:
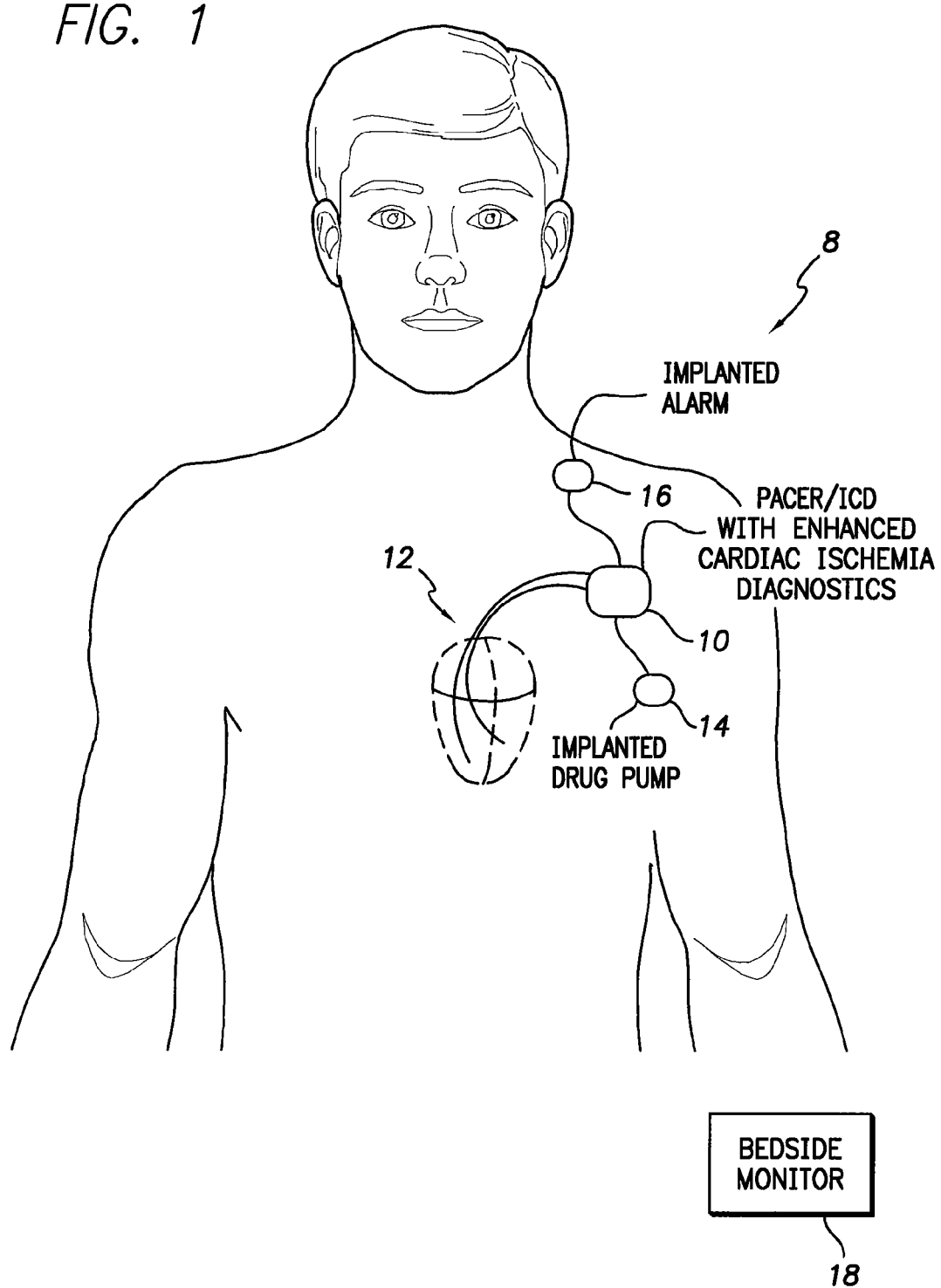
FIG. 1 illustrates pertinent components of an implantable medical system having a pacemaker or ICD capable of generating cardiac ischemia diagnostics taking into account arrhythmia precursors, as well as episodes of sustained arrhythmias, and capable of delivering therapy or warning signals in response thereto.

FIG. 1 illustrates an implantable medical system 8 capable of generating enhanced cardiac ischemia diagnostics for use in determining whether cardiac ischemia within the patient is clinically actionable. System 8 includes a pacer/ICD 10 or other cardiac stimulation device equipped with internal components for generating the enhanced cardiac ischemia diagnostics. In this regard, in addition to detecting cardiac ischemia, the device also detects arrhythmia precursors as well as sustained arrhythmias and generates enhanced diagnostics that correlate the arrhythmia precursors and the sustained arrhythmias with the episodes of cardiac ischemia.

The enhanced diagnostics are primarily provided to help the clinician decide when he or she needs to do something about a patient's worsening ischemia. For example, ischemia that is not too painful or debilitating to the patient but results in an increasing number of PVCs or other arrhythmias may require intervention (i.e., it may be clinically actionable), whereas the same degree of ischemia without the arrhythmias may be deemed as not requiring further intervention. Similarly, when ischemia is only seen in the context of a precursor arrhythmia (e.g., VT or SVT), the physician may choose to treat the VT or SVT to prevent the ischemia, rather than addressing the underlying mechanism of the ischemia directly. In some implementations, it may be appropriate for the device itself to directly warn the patient based on an examination the enhanced diagnostics or to automatically deliver therapy in response to the enhanced diagnostics. Typically, though, such patient warnings or automatic therapy are made in response to the ischemia alone, or the arrhythmia alone, and not necessarily based on a combination of the two. Nevertheless, for the sake of completeness, implementations are described herein where the enhanced diagnostics are employed to directly warn the patient to automatically control therapy.

Figure 8:
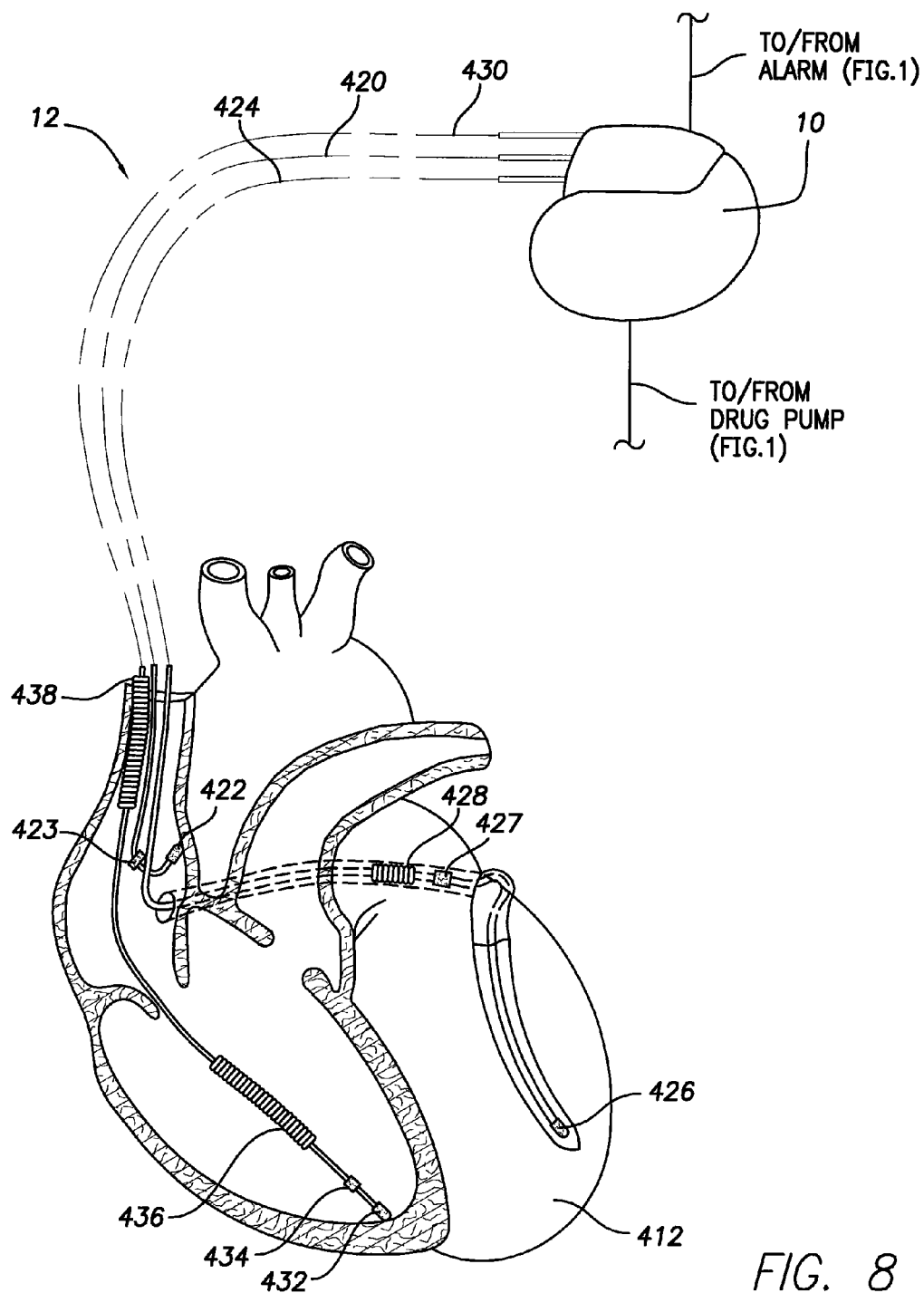
FIG. 8 is a simplified, partly cutaway view, illustrating the pacer/ICD of FIG. 1 along with at full set of leads implanted into the heart of the patient.

To detect cardiac ischemia, pacer/ICD 10 senses IEGM signals or other electrical cardiac signals using a set of cardiac pacing/sensing leads 12 implanted on or within the heart of the patient. (In FIG. 1, only two leads are shown. A full set of leads is illustrated in FIG. 8, described below.) The pacer/ICD analyses the IEGM to detect episodes of ischemia based on deflections in ST segment elevation or using any other appropriate technique. The pacer/ICD also detects arrhythmia precursors and sustained arrhythmias based on an examination of the IEGM signals, again using any appropriate techniques. The pacer/ICD then correlates the arrhythmia precursors and the sustained arrhythmias with the episodes of cardiac ischemia—using techniques to be described in detail below—so as to generate enhanced diagnostics permitting the pacer/ICD itself and/or a physician reviewing the diagnostics to determine whether the ischemia is clinically actionable.

In some implementations, if the ischemia is deemed clinically actionable by the pacer/ICD itself, then appropriate therapy is automatically delivered by the implantable system under the control of the pacer/ICD. For example, anti-thrombolytics or other appropriate medications may be automatically delivered via an implanted drug pump 14, if one is provided. Implantable drug pumps are discussed in U.S. Pat. No. 5,328,460 to Lord, et al., entitled "Implantable Medication Infusion Pump Including Self-Contained Acoustic Fault Detection Apparatus". Warning signals are also generated using either an internal warning device 16 or an external bedside monitor 18 (or other external device) so as to notify the patient and/or a medical professional of cardiac ischemia that warrants clinical intervention. Internal warning device 16 may be a vibrating device or a "tickle" voltage device that, in either case, provides perceptible stimulation to the patient to alert the patient. "Tickle" warning device are also discussed in the Lord, et al. patent. In one implementation, once the patient feels the internal tickle signal, he or she manually places a handheld verification device near his or her chest. The handheld device receives the transmitted signal and provides a confirmation of the warning. In this manner, verification is provided to the patient that the tickle sensation felt internally is indeed a warning of cardiac ischemia and the patient can take immediate and appropriate action. If the patient mistakenly believes that a tickle warning signal has been felt, even though the implanted device has not generated such a warning signal, the handheld verification device will not receive the alarm confirming signal and thus the handheld device will show no warning signal. In this manner, the patient is thereby assured that no warning has been issued. This verification technique is described in detail with U.S. Pat. No. 7,274,959, entitled "System and Method for Detecting Cardiac Ischemia using an Implantable Medical Device", of Wang et al., filed Jun. 24, 2003.

The bedside monitor 18 then provides audible or visual alarm signals (as well as text and graphic displays) to alert the patient and/or medical professional of the clinically actionable ischemia. The bedside monitor may be directly networked with a centralized computing system for immediately notifying a nurse or physician. A system incorporating bedside monitoring units connected to a centralized external programmer system is described in U.S. Pat. No. 6,622,045 to Snell et al., entitled "System and Method for Remote Programming of Implantable Cardiac Stimulation Devices". The enhanced diagnostic information itself is also transmitted to the bedside monitor for relaying to the physician or other medial professional for review to determine whether the ischemia is indeed clinically actionable and, if so, to prescribe appropriate therapies or medications to address the ischemia. Additionally, or alternatively, the diagnostic information is stored within the pacer/ICD for subsequent transmission to an external programmer (not shown in FIG. 1) for review by the physician or other medial professional during a follow-up session with the patient. (An exemplary external programmer is shown in FIG. 10.) The physician may then prescribe appropriate therapies or medications to address the ischemia. The physician may also reprogram the operation of the pacer/ICD to activate, deactivate or otherwise control any therapies that are automatically applied.

Hence, FIG. 1 provides an overview of an implantable system for generating enhanced cardiac ischemia diagnostics and for delivering appropriate warnings and/or therapy. Systems provided in accordance with the invention need not include all the components shown in FIG. 1. In many implementations, for example, the determination of whether ischemia is clinically actionable is made only be the physician based on a review of the enhanced diagnostics via an external programmer. Accordingly, drug pumps and warning devices are not necessarily implanted. Also, the actual generation of the enhanced diagnostics that correlate arrhythmia precursors and arrhythmias with cardiac ischemia may be performed by an external system, such as an external programmer, based on raw data transmitted thereto. Also, systems need not employ both arrhythmia precursors and sustained arrhythmias in the generation of enhance cardiac ischemia diagnostics. Rather, some implementations might generate enhanced ischemia diagnostics using information pertaining to arrhythmia precursors but not actual arrhythmias; whereas other implementations might generate enhanced ischemia diagnostics using information pertaining to actual arrhythmias but not arrhythmic precursors. Note also that, although internal signal transmission lines are illustrated in FIG. 1 for interconnecting the various implanted components, wireless signal transmission may alternatively be employed. The particular sizes, shapes and locations of the implanted components shown in FIG. 1 are merely illustrative and do not necessarily correspond to actual device sizes and shapes or to implant locations.

Ischemia Diagnostic Techniques Incorporating Arrhythmia Precursors

Figure 2:
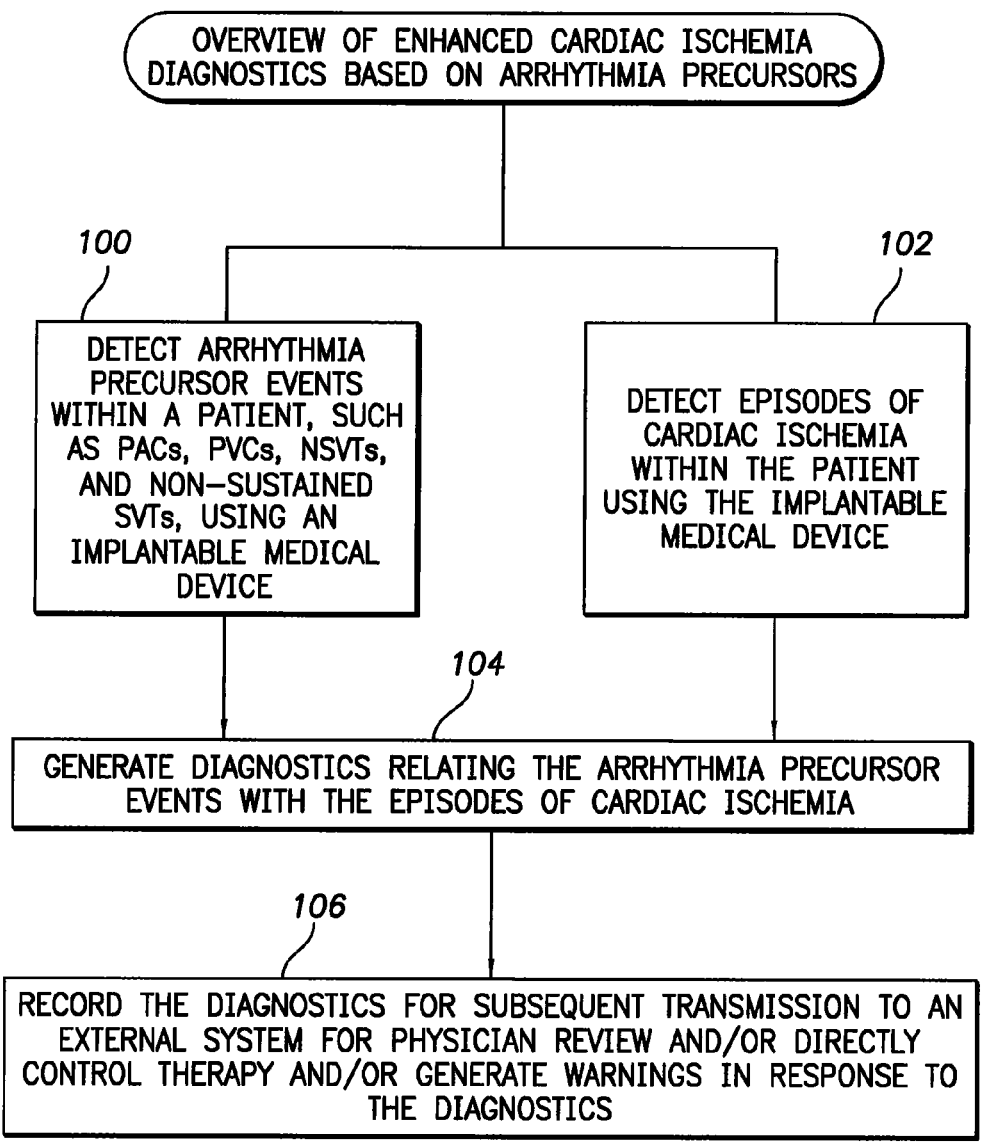
FIG. 2 provides an overview of a technique for generating enhanced cardiac ischemia diagnostics based on arrhythmia precursors, which may be performed by the system of FIG. 1.

FIG. 2 summarizes arrhythmia precursor-based cardiac ischemia diagnostic techniques that may be performed using the system of FIG. 1. Diagnostic techniques exploiting information pertaining to actual arrhythmias are discussed below primarily with reference to FIGS. 4-5. Diagnostic techniques exploiting both arrhythmia precursors and actual arrhythmias are discussed below with reference to FIG. 6. Briefly, beginning at step 100 of FIG. 2, the pacer/ICD detects arrhythmia precursor events within a patient, such as PACs, PVCs, NSVTs, and non-sustained SVTs. The precursor events may include supraventricular events, ventricular events or both. Otherwise conventional techniques for detecting or identifying arrhythmia precursor events may be employed. Note that these events are referred to herein as arrhythmia precursor events because such events often precede a sustained arrhythmia, although they do not necessarily cause the arrhythmia. In some cases, however, precursor events can occur without a subsequent sustained arrhythmia. To distinguish between sustained and non-sustained arrhythmias, the pacer/ICD may be programmed to distinguish between arrhythmias that terminate spontaneously before therapy is delivered and arrhythmias that only terminate in response to therapy, such as arrhythmias that are terminated only in response to anti-tachycardia pacing therapy (ATP), cardioversion shocks, or defibrillation shocks. Arrhythmias that terminate spontaneously before any therapy is delivered are regarded as non-sustained. Arrhythmias that do not terminate until therapy is delivered are regarded as sustained.

At step 102, the pacer/ICD also detects episodes of cardiac ischemia. Again, otherwise conventional techniques for detecting or otherwise identifying episodes of ischemia may be employed such as the ST segment based techniques described within the patents cited above. Non-ST segment-based techniques may additionally or alternatively be employed. See, for example, U.S. Pat. No. 7,274,959, entitled "System and Method for Detecting Cardiac Ischemia Using an Implantable Medical Device", of Wang et al., filed Jun. 24, 2003. Rather than examine the ST segment, the technique of Wang et al. instead examines post-T-wave segments, i.e. that portion of the cardiac signal immediately following the T-wave. In one example, the onset of cardiac ischemia is identified by detecting a sharp falling edge within post-T-wave signals. Another technique for detecting cardiac ischemia based on T-waves is set forth in U.S. Pat. No. 7,225,015, entitled "System and Method for Detecting Cardiac Ischemia based on T-Waves using an Implantable Medical Device", of Min et al., filed Jun. 24, 2003. With the technique of Min et al., cardiac ischemia is detected based either on the total energy of the T-wave or on the maximum slope of the T-wave. A pattern recognition-based technique is described in U.S. patent application Ser. No. 11/394,724 of Ke et al., entitled "System and Method for Detecting Cardiac Ischemia in Real-Time using a Pattern Classifier Implemented within an Implantable Medical Device". See, also, techniques described in U.S. patent application Ser. No. 11/043,612, of Park et al., entitled "System and Method for Distinguishing among Cardiac Ischemia, Hypoglycemia and Hyperglycemia using an Implantable Medical Device".

Next, at step 104, the pacer/ICD generates enhanced diagnostics relating the arrhythmia precursor events with the episodes of cardiac ischemia. In this regard, the pacer/ICD preferably generates (1) diagnostics representative of arrhythmia precursor events occurring during episodes of cardiac ischemia and (2) diagnostics representative of arrhythmia precursor events occurring during periods of time without cardiac ischemia. The diagnostics preferably identify any changes over time in the arrhythmia precursor events, both with regard to precursor events occurring during episodes of cardiac ischemia as well precursor events during periods of time without cardiac ischemia. In particular, the diagnostics preferably identify and track: changes, if any, in a rate at which arrhythmia precursor events occur; changes, if any, in a ratio of lone precursors events to runs of precursor events; changes, if any, in a ratio of arrhythmia precursor events occurring during episodes of ischemia as compared to arrhythmia precursor events occurring during periods of time without ischemia; and changes, if any, in the durations of individual precursor events, such as the durations on NSVT or non-sustained SVT. As will be explained below, the pacer/ICD can be programmed to also take into account the severity of the episodes of ischemia as well as the time of day and other factors.

At step 106, the pacer/ICD then records the diagnostics within internal memory for subsequent transmission to an external system for physician review and/or directly controls therapy and/or generates warning signals in response to the diagnostics. That is, the implanted device controls at least one device function based on the diagnostics, such as recording the diagnostics in memory. As already noted, in some implementations, the pacer/ICD is programmed to evaluate whether the ischemia is clinically actionable based on an examination of the enhanced diagnostics. This evaluation may be performed, for example, by generating a numerical value representative of a likelihood of additional, severe ischemic episodes within the patient and then comparing the value against a threshold representative of a clinically actionable likelihood. The numerical value may be generated, for example, so as to reflect the frequency and severity of episodes of ischemia that have already been detected as well as the frequency and duration of arrhythmia precursor events. Techniques for combining different parameters into a single metric value for threshold comparison are set forth in U.S. Patent Application 2004/0138716, to Koh et al., entitled "System and Method for Detecting Circadian States Using an Implantable Medical Device", published Jul. 15, 2004. In other implementations, the pacer/ICD instead transmits the enhanced diagnostics to an external system for physician review. The physician then determines whether the ischemia is clinically actionable. In still other implementations, the pacer/ICD transmits raw IEGM data to the external system, which generates the enhanced diagnostics.

Within implementations wherein the pacer/ICD itself evaluates whether the ischemia is clinically actionable, the device may immediately control device therapy or other functions if it determines that the ischemia is clinically actionable. For example, the pacer/ICD may be programmed to (1) deactivate overdrive pacing (if it is currently being applied) so as to avoid exacerbating ischemia; (2) deliver anti-thrombolytics or other appropriate medications; and/or (3) pre-charge defibrillation capacitors (if the pacer/ICD is equipped to deliver defibrillation shocks) so as to be prepared in the event a severe ischemia triggers VF. Anti-thrombolytics or other medications may be selectively delivered using the implanted drug pump, if one is provided. Routine experimentation may be employed to identify medications for treatment of cardiac ischemia that are safe and effective for use in connection with an implantable drug pump.

Figure 3:
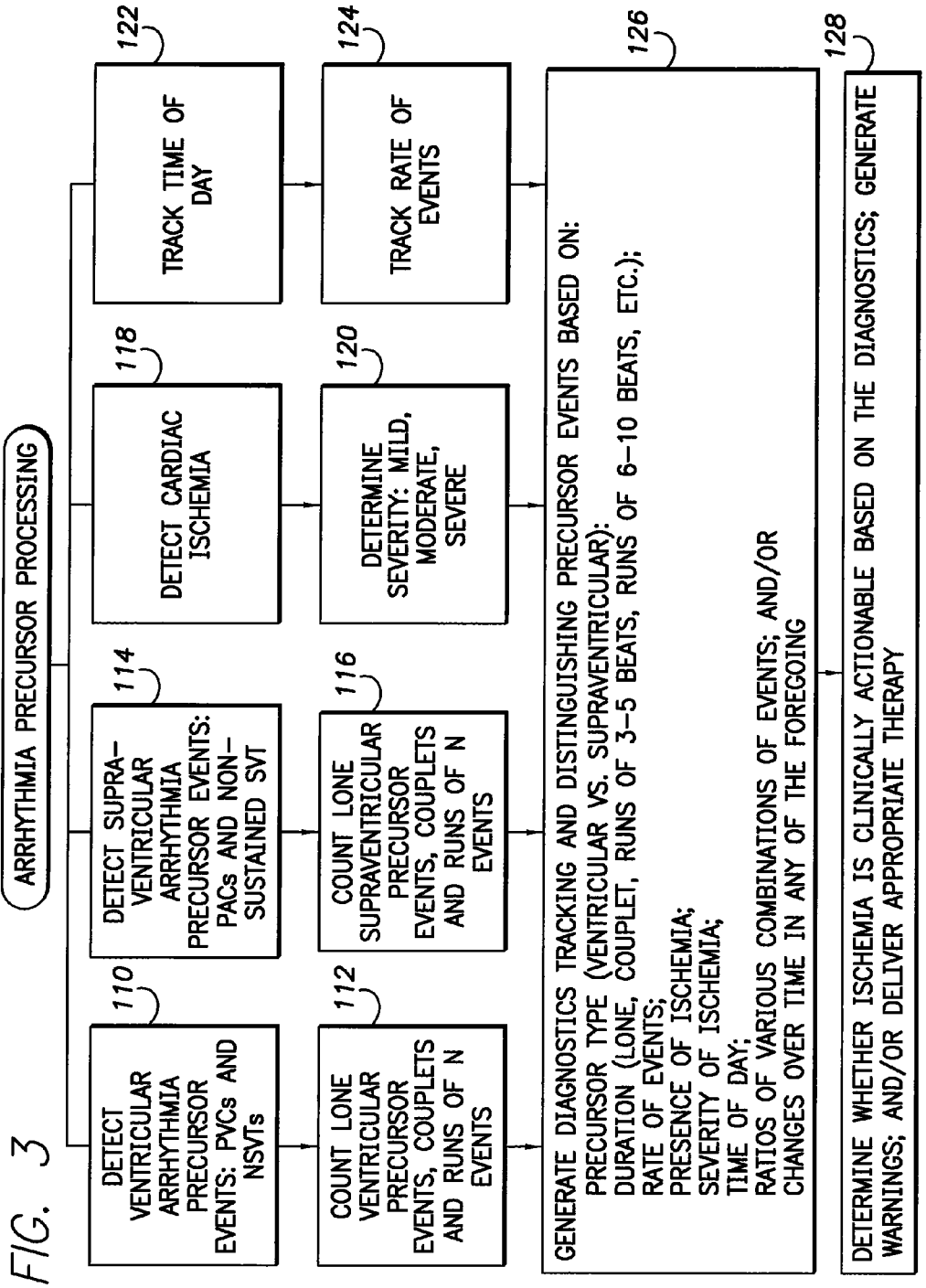
FIG. 3 is a flow diagram illustrating an exemplary embodiment of the technique of FIG. 2.

Turning now to FIG. 3, a more detailed precursor-based diagnostics example is provided, which highlights particular types of arrhythmia precursor diagnostic information that may be collected and correlated. At step 110, pacer/ICD detects ventricular arrhythmia precursor events, particularly: PVCs and NSVTs. At step 112, the pacer/ICD counts lone ventricular precursor events, couplets and runs of N events. A lone PVC is a PVC that is immediately preceded and immediately succeeded by normal paced or sensed ventricular beats. A PVC couplet is a pair of successive PVCs. A run of N PVCs represents N consecutive PVCs without any intervening normal ventricular beats. In one example, for each run of events, the pacer/ICD counts and stores the exact number events in the particular run. In other examples, the pacer/ICD instead increments various bins representative of runs of 3-5 PVCs, 6-10 PVCs, etc. Note that the definition of a "run" is somewhat arbitrary and may include, e.g., any non-sustained rhythm including couplets, NSVTs, etc. In the particular implementations described herein, runs comprise three or more events of a non-sustained rhythm. Other implementations can differ in terminology or classification schemes.

Concurrently, the pacer/ICD, at step 114, detects supraventricular arrhythmia precursor events (particularly PACs and non-sustained SVTs) and, at step 116, counts lone supraventricular precursor events, couplets and runs of N events. The same considerations regarding lone events, couplets and runs of events discussed with regard to the ventricular precursor events applies to supraventricular events as well. That is, the distinction typically only applies to discrete precursors such as PACs. The pacer/ICD also, at step 118, detects episodes of cardiac ischemia and, at step 120, evaluates the severity of the ischemia: mild, moderate or severe. In this regard, cardiac ischemia may be detected by tracking at least one morphological value representative of a likelihood of an ischemic episode (such as a change in ST segment elevation) and determining whether the value exceeds a predetermined threshold representative of an on-going ischemic episode. The severity of the ischemia may be evaluated by comparing the value against additional, higher thresholds, representative of more significant changes in the morphological parameters. In some examples, several different morphological parameters are evaluated both for the purposes of detecting ischemia and for evaluating its severity, including parameters other than ST segments. Examples of non-ST segment-based examples are discussed in the various patents cited above. In other implementations, the severity of the ischemia is merely rated as mild or severe. In still other implementations, a greater number of severity classifications are employed. At step 122, the pacer/ICD also tracks the time of day and, at step 124, evaluates the rate of precursor events detected at steps 110 and 114, i.e. the rate at which individual PVCs or PACs occur or the rate at which NSVTs or non-sustained SVTs occur, i.e. ten PVCs per hour, or five episodes of non-sustained SVT per day, etc.

At step 126, the pacer/ICD then generates diagnostics tracking and distinguishing supraventricular and ventricular precursor events based on one or more of: precursor type (ventricular vs. supraventricular); precursor duration (lone, couplet, runs of 3-5 beats, runs of 6-10 beats, etc.); rate of precursor events; presence of ischemia; severity of ischemia; the time of day at which the ischemia and/or the precursor events occurred; ratios of various combinations of precursor events and ischemias; and/or changes over time in any of the foregoing. Preferably, the pacer/ICD specifically detects each of the following, if occurring within the patient: a change in the severity of arrhythmia precursor events over time; a change in the severity of episodes of cardiac ischemia over time; a ratio of the severity of arrhythmia precursor events to the severity of episodes of cardiac ischemia; and a change in a distribution of the severity of episodes of cardiac ischemia over time. The diagnostics that are generated specifically highlight these factors, as they are likely to be of particular importance in determining whether the ischemia within the patient is clinically actionable.

At step 128, the pacer/ICD then determines whether the ischemia is clinically actionable based on the diagnostics; generate warnings; and/or delivers appropriate therapy, as already discussed. Also, as already noted, depending upon the implementation, the determination of whether the ischemia is clinically actionable may be deferred to the physician or other medical professional reviewing the diagnostic data.

Diagnostic Techniques Distinquishing Pre- and Post-Ischemia Arrhythmias

Figure 4:
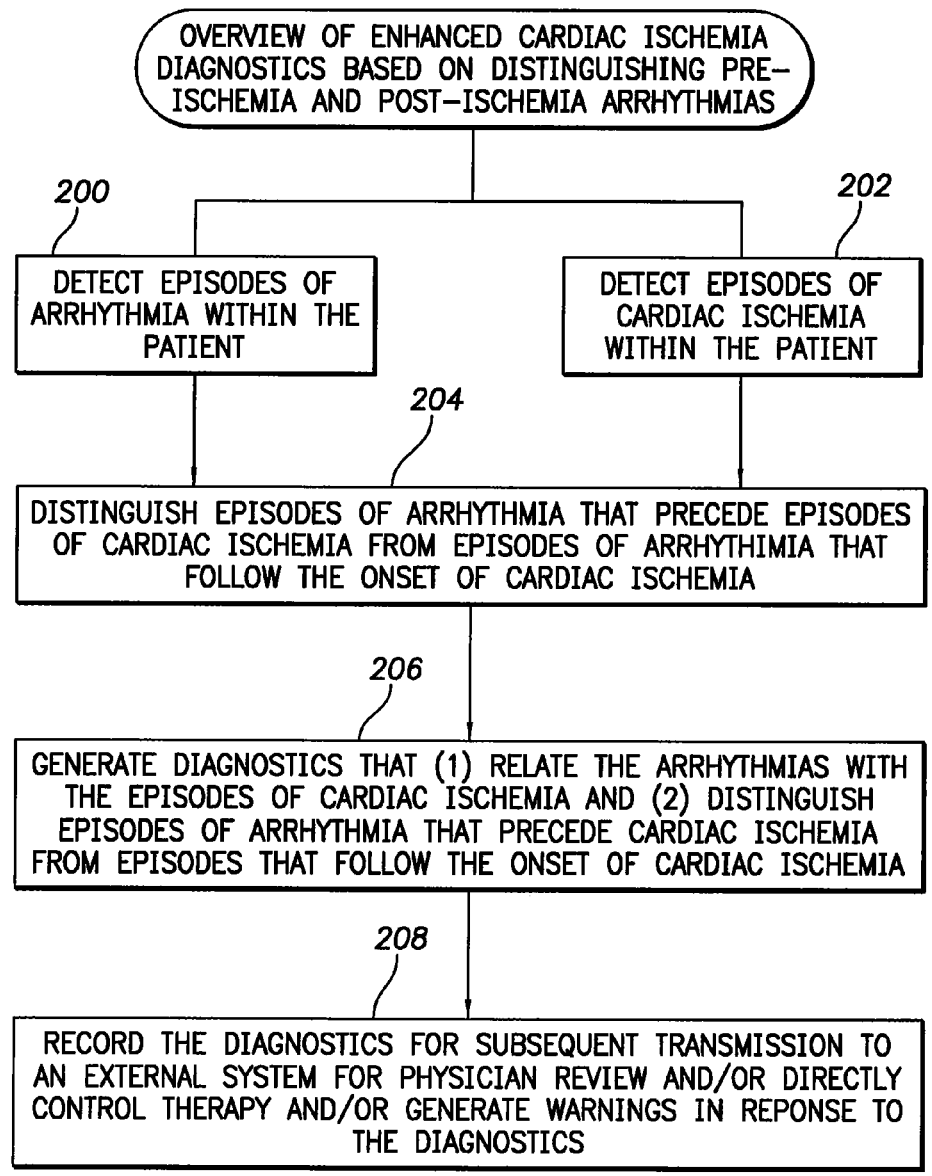
FIG. 4 provides an overview of a technique for generating enhanced cardiac ischemia diagnostics based on distinguishing pre- and post-ischemia arrhythmias, which may be performed by the system of FIG. 1.
Figure 5:
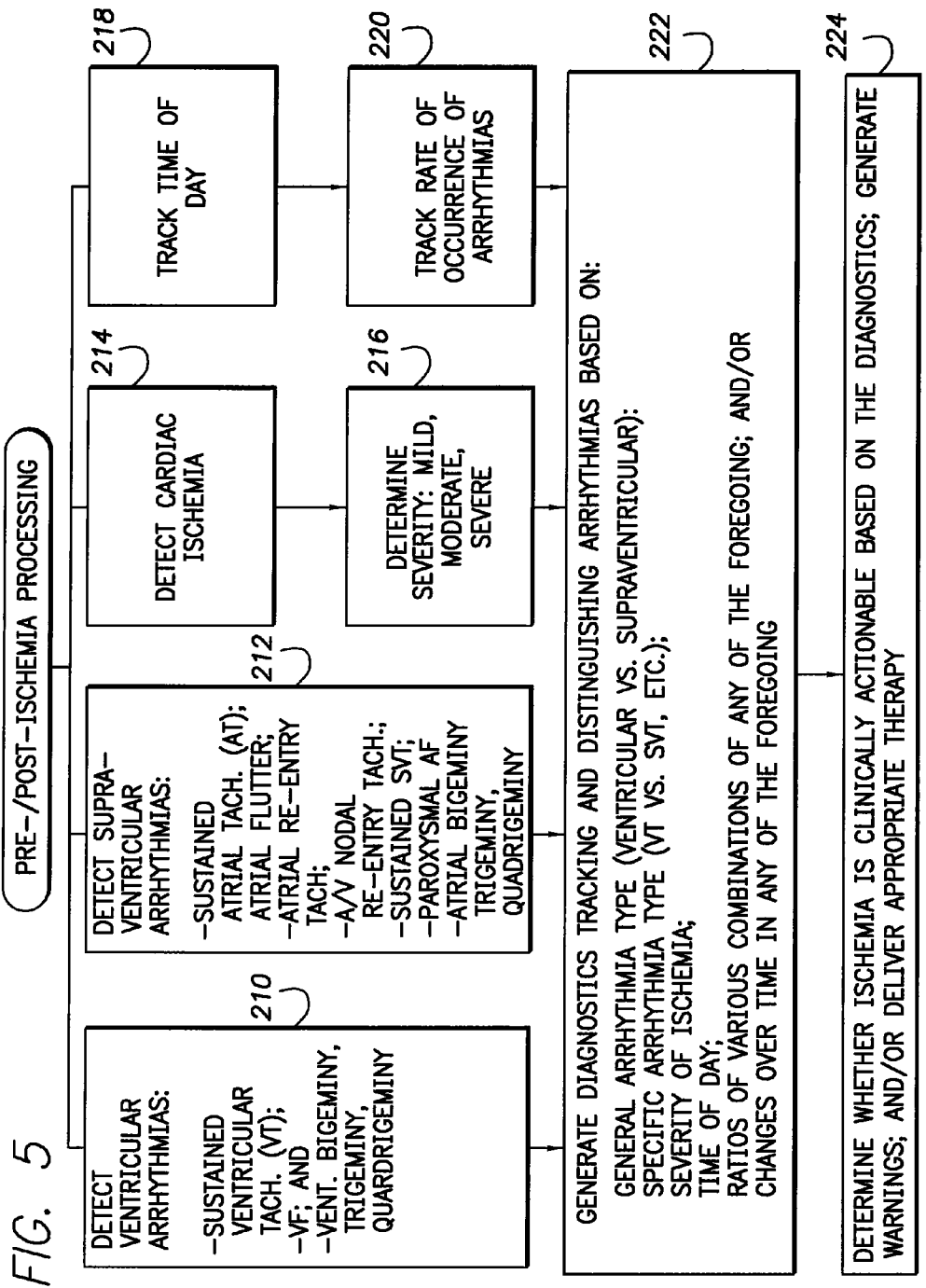
FIG. 5 is a flow diagram illustrating an exemplary embodiment of the technique of FIG. 4.

Turning now to FIGS. 4 and 5, diagnostic techniques that distinguish between arrhythmias preceding an ischemia and arrhythmias following an ischemia will be described. FIG. 4 provides an overview of the techniques. A more detailed example is set forth in FIG. 5. Briefly, beginning at step 200 of FIG. 4, the pacer/ICD detects episodes of sustained supraventricular and/or ventricular arrhythmia within the patient. The discussions provided above regarding the distinction between sustained and non-sustained arrhythmias are applicable here as well. Examples of sustained "ventricular" arrhythmias include: sustained VT; sustained SVT; VF; and sustained episodes of ventricular bigeminy, trigeminy, quadrigeminy, etc. Examples of sustained "supraventricular arrhythmias" include: sustained AT; AF; atrial flutter; atrial reentry tachycardia; atrioventricular (A/V) nodal reentry tachycardia; paroxysmal AF; and sustained atrial bigeminy, trigeminy, quadrigeminy, etc. Otherwise conventional techniques for detecting or distinguishing among various sustained arrhythmias may be employed. Note that the classification of supraventricular vs. ventricular is somewhat arbitrary and other classification schemes may be employed. In some implementations, it may be appropriate to provide additional designations beyond "supraventricular" and "ventricular," such as a separate "atrial" category of arrhythmias.

At step 202, the pacer/ICD also detects episodes of cardiac ischemia. As before, otherwise conventional techniques for detecting or identifying episodes of ischemia may be employed. At step 204, the pacer/ICD distinguishes episodes of arrhythmia that precede episodes of cardiac ischemia (i.e. arrhythmias that might be a proximate cause of the ischemia) from episodes of arrhythmia that follow episodes of cardiac ischemia (i.e. arrhythmias that might have been caused by the ischemia). In one example, a predetermined time window is employed to determine whether a particular arrhythmia is pre- or post-ischemia. If an ischemia is detected within the time window following a sustained arrhythmia, the arrhythmia is deemed to precede the ischemia. Conversely, if an arrhythmia is detected within the time window following the onset of an episode of ischemia, the arrhythmia is deemed to follow the ischemia. Hence, if the time window is five minutes, then any arrhythmia occurring within the time interval beginning five minutes before the onset of an episode of ischemia is regarded as preceding the ischemia, i.e. it is pre-ischemia. Any arrhythmia occurring within the time interval beginning at the onset of the arrhythmia and ending five minutes after the end of the episode of ischemia is regarded as being post-ischemia. Any arrhythmia not occurring within the time window before or after an ischemia is therefore neither pre-ischemia nor post-ischemia. In some cases, multiple arrhythmias may "precede" a single episode of ischemia. Likewise, multiple arrhythmias may "follow" the onset of a single episode of ischemia. If two or more episodes of ischemia occur in close succession, a single episode of arrhythmia may be regarded as both preceding one episode of ischemia and following another episode of ischemia. As can be appreciated, a determination of whether an episode of arrhythmia is pre-ischemia is not made in real-time but is instead made upon detection of the subsequent episode of ischemia.

Next, at step 206, the pacer/ICD generates enhanced diagnostics that (1) relate the various detected arrhythmias with the episodes of cardiac ischemia and (2) distinguish episodes of arrhythmia that precede cardiac ischemia from episodes that follow cardiac ischemia. As with the various embodiments discussed above, the pacer/ICD can additionally take into account the severity of the episodes of ischemia as well as the time of day when ischemia occurred.

At step 208, the pacer/ICD then records the diagnostics for subsequent transmission to an external system for physician review and/or directly controls therapy and/or generates warnings in response to the diagnostics. That is, the implanted device again controls at least one device function based on the diagnostics. In some implementations, the pacer/ICD is programmed to evaluate whether the ischemia is clinically actionable based on an examination of the enhanced diagnostics generated at step 206 and to deliver therapy accordingly. In other implementations, the pacer/ICD instead transmits the enhanced diagnostics to an external system so that a physician can then determine whether the ischemia is clinically actionable. In still other implementations, the pacer/ICD transmits raw IEGM data covering periods of time with episodes of ischemia and episodes of pre- or post-ischemia arrhythmia to the external system, which generates the enhanced diagnostics of step 206.

Turning now to FIG. 5, a more detailed example is provided that highlights particular types of pre- and post-ischemia diagnostic information that may be collected and correlated. At step 210, pacer/ICD detects various ventricular arrhythmias such as sustained VT; and VF. Concurrently, the pacer/ICD, at step 212, detects sustained supraventricular arrhythmias such as sustained SVT; sustained AT; AF; and atrial flutter. The pacer/ICD also, at step 214, detects episodes of cardiac ischemia and, at step 216, evaluates its severity. At step 218, the pacer/ICD also tracks the time of day and, at step 220, evaluates the rate of arrhythmias detected at steps 210 and 212, i.e. the rate at which individual episodes of sustained arrhythmia occur over time, i.e. one sustained arrhythmia per hour, or one per day, etc.

At step 222, the pacer/ICD then generates diagnostics tracking and distinguishing supraventricular and ventricular sustained arrhythmias based on one or more of: general arrhythmia type (ventricular vs. supraventricular); specific arrhythmia type (VT vs. SVT, etc.); severity of ischemia; time of day; ratios of various combinations of any of the foregoing; and/or changes over time in any of the foregoing. Preferably, the pacer/ICD specifically detects each of the following, if occurring within the patient: changes in the rate at which sustained arrhythmias occur; changes in the ratio of sustained arrhythmias that precede ischemia to those that follow ischemia; and changes in the durations of sustained arrhythmias over time. The diagnostics that are generated specifically highlight these factors, as they are likely to be of particular importance in determining whether the ischemia within the patient is clinically actionable. At step 224, a determination is made as to whether the ischemia is clinically actionable based on the diagnostics. Typically, this determination is made by a physician. If properly equipped, though, the pacer/ICD can make the determination based on an analysis of the diagnostics and, if so, can generate warnings and/or deliver appropriate therapy in response thereto, as already discussed.

Combined Diagnostics

Figure 6:
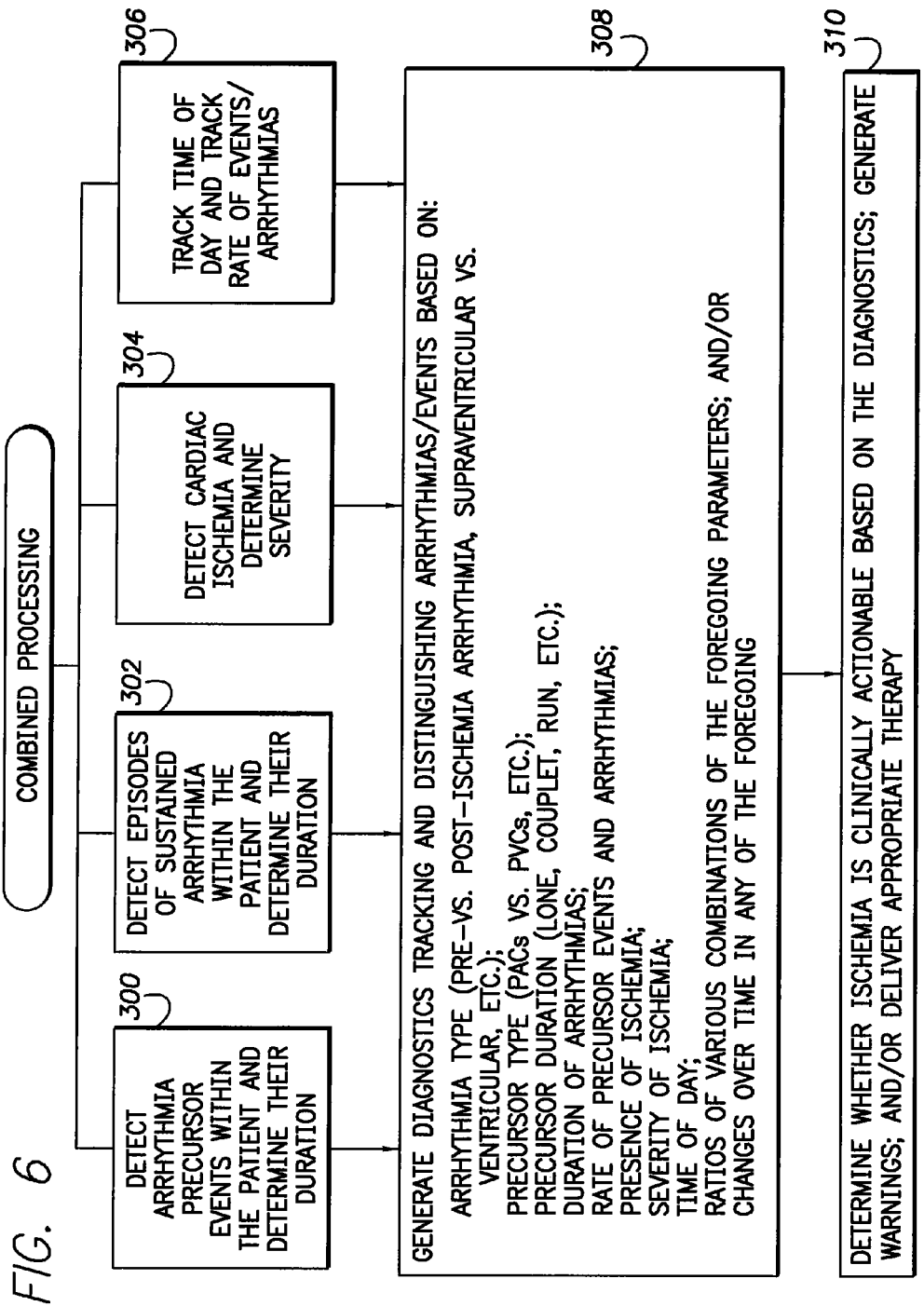
FIG. 6 is a flow diagram illustrating an exemplary combined embodiment incorporating the techniques of FIGS. 2-5.

Preferably, information pertaining both to the arrhythmia precursors of FIGS. 2-3 and to the pre- and post-ischemia arrhythmias of FIGS. 4-5 are tracked to generate comprehensive, enhanced ischemia diagnostics. This is illustrated within FIG. 6. Many of the steps of FIG. 6 are similar to corresponding steps of FIGS. 3 and 5 and will only be briefly summarized. At step 300, the pacer/ICD detects arrhythmia precursor events within the patient and determines their duration while, at step 302, also detecting episodes of sustained arrhythmia within the patient and determining their duration. At step 304, the pacer/ICD detects episodes of cardiac ischemia and determines its severity while, at step 306, also tracking the time of day and tracking rate of the various events/arrhythmias detected at steps 300 and 302. At step 308, the pacer/ICD then generates diagnostics tracking and distinguishing arrhythmias/events based on one or more of: arrhythmia type (pre- vs. post-ischemia arrhythmia, supraventricular vs. ventricular, etc.); precursor type (PACs vs. PVCs, etc.); precursor duration (lone, couplet, run, etc.); arrhythmia duration; rate of precursor events and arrhythmias; presence of ischemia; severity of ischemia; time of day; ratios of various combinations of the foregoing parameters; and/or changes over time in any of the foregoing. Still other types of data may be incorporated into the enhanced diagnostics. For example, cardiac workload may be detected and correlated with cardiac ischemia.

At step 310, a determination is made as to whether the ischemia is clinically actionable based on the diagnostics. As already discussed, this determination is typically made by a physician. If properly equipped, though, the pacer/ICD can make the determination based on an analysis of the diagnostics and generate warnings and/or deliver appropriate therapy in response thereto.

The pacer/ICD then determines whether the ischemia is clinically actionable based on the diagnostics; generates warnings; and/or delivers appropriate therapy, as already discussed. Also, as with the preceding embodiments, depending upon the particular implementation, the determination of whether the ischemia is clinically actionable may be deferred to the physician or other medical professional reviewing the diagnostic data. That is, the enhanced diagnostic data is sent to an external display device, such as an external programmer, for display.

Figure 7:
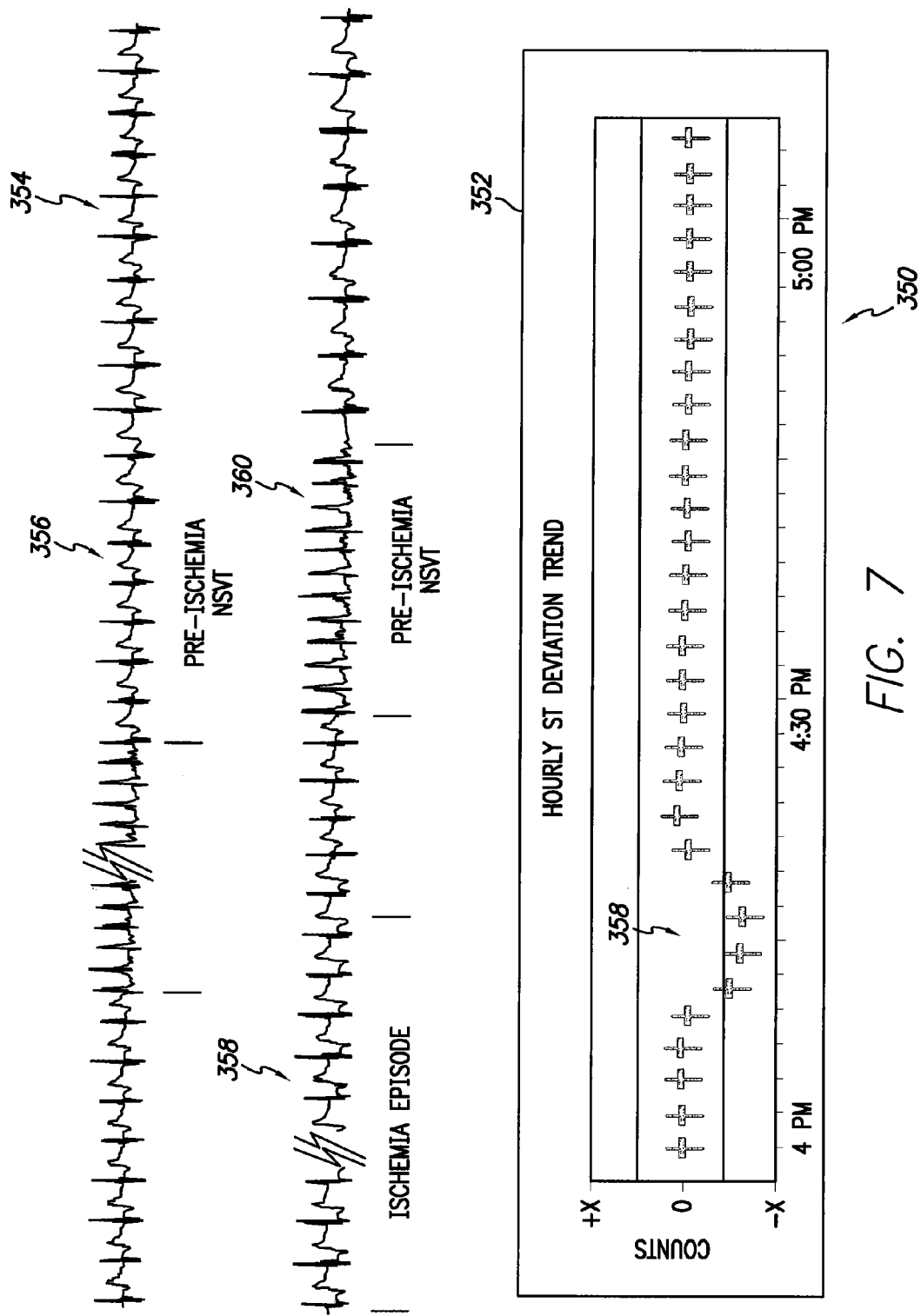
FIG. 7 is a graphical illustration of an exemplary diagnostics display incorporating information generated using the techniques of FIGS. 2-6.

FIG. 7 provides an exemplary "screen shot" of an enhanced cardiac ischemia diagnostics display that might be displayed by an external programmer illustrating the presentation of diagnostic data incorporating cardiac ischemia and pre- and post-ischemia arrhythmias. More specifically, exemplary display 350 provides a graph of hourly ST deviation level 352 (which may be based, for example, on ST segment shift). The display also provides an IEGM 354 and particularly identifies any arrhythmias detected therein. In this example, the IEGM is displayed on two lines, with the second line being a continuation of the first. Also, note that the ST deviation graph covers about an hour's worth of data. The IEGM display highlights only pertinent portions of the corresponding IEGM data, with interrupt markers indicting where data is truncated. The display also specifically indicates whether the arrhythmias detected therein were deemed to be "pre-ischemia" arrhythmias or "post-ischemia" arrhythmias. In this example, one pre-ischemia NSVT 356 has been detected prior to an ischemic episode 358 that was precipitated by the NSVT. Also, one post-ischemia NSVT 360 has been detected following the ischemic episode. The ischemia episode 358 is also identified within the ST deviation trend graph. The episode of ischemia lasted about ten minutes. As can be appreciated, only a small portion of the corresponding IEGM data for that ten minute interval is displayed within IEGM graph 354.

FIG. 7 provides just one type of sample display. Numerous others are accommodated by the invention. In particular, whereas FIG. 7 illustrates data graphically, numerous other displays may be generated wherein data is tabulated in tables or histograms so as to indicate, e.g., the relative numbers of pre-ischemia vs. post-ischemia arrhythmias, or the relative numbers of different types of arrhythmia precursors, their rates, etc. as already explained.

What have been described are various techniques for generating and exploiting enhanced diagnostics information pertaining to cardiac ischemia. As noted, the diagnostics may be generated within a pacer/ICD for transmission to an external programmer for display or may be generated by the external programmer itself. For the sake of completeness, descriptions of an exemplary pacer/ICD and an exemplary external programmer will now be provided. The techniques of the invention, however, may be performed using any suitable implantable and external components.

Exemplary Pacer/ICD

FIG. 8 provides a simplified block diagram of the pacer/ICD of FIG. 1, which is a dual-chamber stimulation device capable of treating both fast and slow arrhythmias with stimulation therapy, including cardioversion, defibrillation, and pacing stimulation, as well as capable of generating the enhanced cardiac ischemia diagnostics and controlling the delivery of therapy and warnings in response thereto. To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 9:
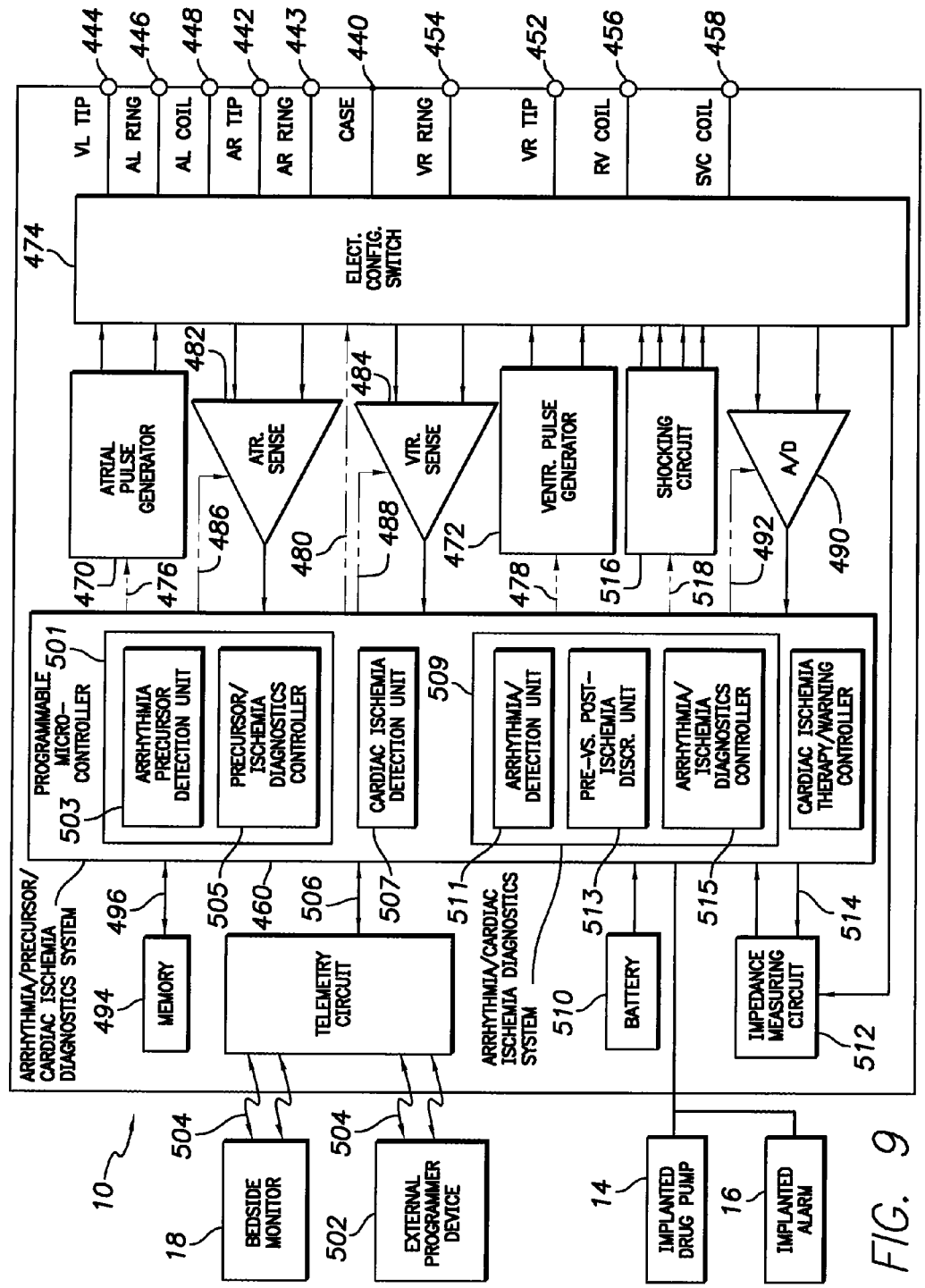
FIG. 9 is a functional block diagram of the pacer/ICD of FIG. 8, illustrating basic circuit elements that provide cardioversion, defibrillation and/or pacing stimulation in the heart and particularly illustrating components for generating cardiac ischemia diagnostics and for controlling delivery of therapy or warning signals in response thereto in accordance with the techniques of FIGS. 1-6.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned ischemia diagnostics. The housing 440 for pacer/ICD 10, shown schematically in FIG. 9, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial tip electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry.

Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 9, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain control and/or automatic sensitivity control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer or bedside monitor 18. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 502 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV Delay, V-V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes at least one battery 510 of other power source, which provides operating power to all of the circuits shown in FIG. 9. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 10 is preferably capable of high voltage therapy and appropriate batteries.

As further shown in FIG. 9, pacer/ICD 10 includes an impedance measuring circuit 512 that is enabled by the microcontroller 460 via a control signal 514. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 512 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Microcontroller 460 also includes various components directed to the detecting cardiac ischemia, arrhythmic precursors, and sustained arrhythmias, for generating enhanced diagnostics based on the detected information, and for controlling delivery of therapy and warnings in response thereto. In particular, the microcontroller includes an arrhythmia precursor/cardiac ischemia diagnostics system 501 operative to generate diagnostics relating arrhythmia precursor events with episodes of cardiac ischemia within the patient, in accordance with techniques already described. The diagnostics system 501 includes an arrhythmia precursor detection unit 503 operative to detect arrhythmia precursor events within the patient and an arrhythmia precursor/cardiac ischemia diagnostics controller 505 operative to generate diagnostics relating arrhythmia precursor events with episodes of cardiac ischemia detected by a cardiac ischemia detection unit 507. The microcontroller also includes an arrhythmias/cardiac ischemia diagnostics system 509 operative to generate diagnostics relating pre-ischemia arrhythmias and post-ischemia arrhythmias with episodes of cardiac ischemia within the patient, again in accordance with techniques already described. The diagnostics system 509 includes an arrhythmia detection unit 511 operative to detect episodes of arrhythmia within the patient, a pre-ischemia/post-ischemia distinguishing unit 513 operative to distinguish episodes of arrhythmia that precede episodes of cardiac ischemia from episodes of arrhythmia that follow episodes of cardiac ischemia, and an arrhythmia/cardiac ischemia diagnostics controller 515 operative to generate diagnostics relating the arrhythmias with the episodes of cardiac ischemia and distinguishing episodes of arrhythmia that precede cardiac ischemia from episodes that follow cardiac ischemia.

A cardiac ischemia therapy/warning controller 517 controls delivery of therapy and/or warning signals in response to the enhanced diagnostics, again in accordance with techniques already described. In particular, the therapy/warning controller 517 may be equipped to evaluate whether ischemia within the patient is clinically actionable and, if so, to control implanted drug pump 14 or implanted alarm 16 accordingly, again in accordance with techniques already described. The diagnostics generated by diagnostics systems 501 and 509 are preferably also recorded within memory 494 for subsequent transmission to either bedside monitor 18 or external programmer 502. In other implementations, no therapy/warning controller is provided within the pacer/ICD.

The determination of whether ischemia within the patient is clinically actionable is instead performed by physician based on the diagnostics data transmitted from the pacer/ICD to the external system. In still other implementations, the pacer/ICD transmits IEGM data to the external system, which generates the enhanced diagnostics.

Depending upon the implementation, the various components of the microcontroller may be implemented as separate software modules or the modules may be combined to permit a single module to perform multiple functions. In particular, diagnostics systems 501 and 509 may be implemented as a single combined diagnostics system operative to generate diagnostics relating the arrhythmia precursor events and the arrhythmias with the episodes of cardiac ischemia and also distinguishing episodes of arrhythmia that precede cardiac ischemia from episodes that follow cardiac ischemia. In addition, although shown as being components of the microcontroller, some or all of these components may be implemented separately from the microcontroller as hardware or firmware devices.

Exemplary External Programmer

FIG. 10 illustrates pertinent components of an external programmer 502 for use in programming pacer/ICD 10 of FIG. 9 and for performing the above-described ischemia diagnostic processing techniques if the pacer/ICD is not equipped to perform those techniques itself. For the sake of completeness, other device programmer functions are also described. Generally, the programmer permits a physician or other user to program the operation of the implanted device and to retrieve and display information received from the implanted device such as IEGM data and device diagnostic data. Additionally, the external programmer can be optionally equipped to receive and display EKG data from separate external EKG leads that may be attached to the patient. Depending upon the specific programming of the external programmer, programmer 502 may also be capable of processing and analyzing data received from the implanted device and from the EKG leads to, for example, render preliminary diagnosis as to medical conditions of the patient or to the operations of the implanted device.

Now, considering the components of programmer 502, operations of the programmer are controlled by a CPU 602, which may be a generally programmable microprocessor or microcontroller or may be a dedicated processing device such as an application specific integrated circuit (ASIC) or the like. Software instructions to be performed by the CPU are accessed via an internal bus 604 from a read only memory (ROM) 606 and random access memory 630. Additional software may be accessed from a hard drive 608, floppy drive 610, and CD ROM drive 612, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 614 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 616 overlaid on the LCD display or through a standard keyboard 618 supplemented by additional custom keys 620, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 502 to retrieve data stored within any implanted devices and to also retrieve EKG data from EKG leads, if any, coupled to the patient. To this end, CPU 602 transmits appropriate signals to a telemetry subsystem 622, which provides components for directly interfacing with the implanted devices, and the EKG leads. Telemetry subsystem 622 includes its own separate CPU 624 for coordinating the operations of the telemetry subsystem. Main CPU 602 of programmer communicates with telemetry subsystem CPU 624 via internal bus 604. Telemetry subsystem additionally includes a telemetry circuit 626 connected to telemetry wand 628, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 634 for receiving surface EKG signals from a surface EKG system 632. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. The patient diagnostics data can also includes information pertaining to arrhythmia precursor events and to episodes of cardiac ischemia detected within the patient by the implanted device.

The patient diagnostics data can also include information pertaining to arrhythmias and to episodes of cardiac ischemia detected within the patient by the implanted device, as well as information distinguishing episodes of arrhythmia that precede episodes of cardiac ischemia from episodes of arrhythmia that follow episodes of cardiac ischemia. That is, the telemetry system is operative to receive: information pertaining to arrhythmia precursor events and to episodes of cardiac ischemia detected within the patient by the implanted device;

information pertaining to arrhythmias and to episodes of cardiac ischemia detected within the patient by the implanted device; and information distinguishing episodes of arrhythmia that precede episodes of cardiac ischemia from episodes of arrhythmia that follow episodes of cardiac ischemia.

Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 502 either within a random access memory (RAM) 630, hard drive 608 or within a floppy diskette placed within floppy drive 610. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 502, the implanted devices may be further controlled to transmit additional data in real time as it is detected by the implanted devices, such as additional IEGM data, lead impedance data, and the like. Additionally, or in the alternative, telemetry subsystem 622 receives EKG signals from EKG leads 632 via an EKG processing circuit 634. As with data retrieved from the implanted device itself, signals received from the EKG leads are stored within one or more of the storage devices of the external programmer. Typically, EKG leads output analog electrical signals representative of the EKG. Accordingly, EKG circuit 634 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 602, the programming commands are converted to specific programmable parameters for transmission to the implanted devices via telemetry wand 628 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 636.

Additionally, CPU 602 also preferably includes a programmer-based arrhythmia precursor/cardiac ischemia diagnostics controller 646, which is operative to generate diagnostics relating arrhythmia precursor events with the episodes of cardiac ischemia as described above in connection with FIGS. 2-3. The CPU also includes a programmer-based arrhythmia/cardiac ischemia diagnostics controller 647, which is operative to generate diagnostics relating arrhythmias with the episodes of cardiac ischemia and distinguishing episodes of arrhythmia that precede cardiac ischemia from episodes that follow cardiac ischemia, as described above in connection with FIGS. 5-6. Together the two diagnostics controllers can generate combined diagnostics of the type described above with reference to FIGS. 6-7. LCD display 614 displays the diagnostics generated by the diagnostics controllers. Additionally, the diagnostics are output via printer 636 or any of the other output devices of FIG. 10 and/or stored via any of the storage devices shown. If the pacer/ICD generates the ischemia diagnostics itself for transmission to the external programmer, then diagnostics controllers of the external programmer coordinate the display of the diagnostics, as well as its storage or further outputting.

Programmer/monitor 502 also includes a modem 638 to permit direct transmission of data to other programmers via the public switched telephone network (PSTN) or other interconnection line, such as a T1 line or fiber optic cable. Depending upon the implementation, the modem may be connected directly to internal bus 604 may be connected to the internal bus via either a parallel port 640 or a serial port 642. Other peripheral devices may be connected to the external programmer via parallel port 640 or a serial port 642 as well. Although one of each is shown, a plurality of input output (10) ports might be provided. A speaker 644 is included for providing audible tones to the user, such as a warning beep in the event improper input is provided by the physician. Telemetry subsystem 622 additionally includes an analog output circuit 645 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 10 are intended merely to provide an overview of the operation of programmer and are not intended to describe in detail every feature of the hardware and software of the programmer and is not intended to provide an exhaustive list of the functions performed by the programmer.

In general, the various functional components of the exemplary systems described herein may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention. Note also that the term "including" as used herein is intended to be inclusive, i.e. "including but not limited to".

What is claimed is:

1. A method for use with an implantable medical device for implant within a patient, comprising:
   detecting arrhythmia precursor events within the patient wherein the arrhythmia precursor events comprise one or more of premature ventricular contractions and episodes of non-sustained ventricular tachycardia;
   detecting episodes of cardiac ischemia within the patient;
   generating diagnostics relating the arrhythmia precursor events with the episodes of cardiac ischemia and distinguishing clinically actionable ischemia events from non-clinically actionable ischemia events; and
   controlling at least one device function based on the diagnostics, wherein the at least one device function comprising generating a warning signal if the episodes of cardiac ischemia happen absent one or more arrhythmia precursor events corresponding with the non-clinically actionable ischemia events, and a second therapy based function different from the first function if the episodes of cardiac ischemia happen coincident with one or more arrhythmia precursor events corresponding with the clinically actionable ischemia events.

2. The method of claim 1 wherein detecting arrhythmia precursor events within the patient includes detecting on one or more supraventricular arrhythmia precursors including premature atrial contractions (PACs) and episodes of non-sustained supraventricular tachycardia (SVT).

3. The method of claim 1 wherein detecting arrhythmia precursor events within the patient further includes detecting and distinguishing lone precursor events, couplets of precursor events and runs of precursor events having three or more events in sequence.

4. The method of claim 1 wherein detecting episodes of cardiac ischemia within the patient includes detecting at least one morphological value representative of a likelihood of an ischemic episode and determining whether the value exceeds at least one predetermined threshold representative of an ischemic episode.

5. The method of claim 1 wherein generating diagnostics relating arrhythmia precursor events with episodes of cardiac ischemia includes generating diagnostics representative of arrhythmia precursor events occurring during episodes of cardiac ischemia, and generating diagnostics representative of arrhythmia precursor events occurring during periods of time without cardiac ischemia.

6. The method of claim 1 wherein controlling at least one device function based on the diagnostics includes one or more of: controlling the recording of the diagnostics within the device and controlling the transmission of the diagnostics to an external device.

7. The method of claim 1 wherein controlling at least one device function based on the diagnostics includes controlling therapy delivered to the patient by the implanted device.

* * * * *